United States Patent [19]

de Jongh

[11] 3,998,813

[45] Dec. 21, 1976

[54] PROCESS FOR THE PREPARATION OF 11β-HYDROXY-18-ALKYL-ESTRANE COMPOUNDS

[75] Inventor: Hendrik Paul de Jongh, Oss, Netherlands

[73] Assignee: Akzona Incorporated, Asheville, N.C.

[22] Filed: June 30, 1975

[21] Appl. No.: 591,979

[52] U.S. Cl. .................. 260/239.55 C; 195/51 S; 260/397.45
[51] Int. Cl.² .......................................... C07J 5/00
[58] Field of Search ............ 260/239.55 C, 397.45

[56] References Cited
UNITED STATES PATENTS

| | | | |
|---|---|---|---|
| 3,927,046 | 12/1975 | van den Broek | 260/397.3 |
| 3,928,326 | 12/1975 | Brattsand et al. | 260/397.45 |

Primary Examiner—Elbert L. Roberts
Attorney, Agent, or Firm—Francis W. Young; Philip M. Pippenger; Hugo E. Weisberger

[57] ABSTRACT

The present invention relates to a novel process for the preparation of 11β-hydroxy-18-alkyl-estrane compounds by reacting an 11β-hydroxy-13-methyl-gonane compound with an acylhypoiodite to give an 11β-hydroxy-13-iodomethyl-gonane compound and reacting the latter compound with an alkylhalide in the presence of an alkali metal or with an alkali metal alkyl compound or with dimethylformamide in the presence of an alkali metal alkyl compound followed by a treatment with a proton donor, whereafter in the latter case the 18-methyl compound or is reacted with a trialkyl- or triaryl-alkylidene phosphorane (Wittig reagent), followed by a reduction of the thus-obtained 18-alkenyl compound to the corresponding 18-alkyl-compound, and to novel intermediates of the subject compounds.

20 Claims, No Drawings

PROCESS FOR THE PREPARATION OF 11β-HYDROXY-18-ALKYL-ESTRANE COMPOUNDS

The present invention relates to a novel process for the preparation of 11β-hydroxy-18-alkyl-estrane compounds and novel intermediates thereof.

18-Alkyl-estrane compounds are pharmacologically important 19-nor-steroids. An example of such a compound is norgestrel (= 17α-ethinyl-17β-hydroxy-18-methyl-Δ⁴-estren-3-one) which has found application as an oral progestative and is used i.a. as progestational constituent in contraceptives. In literature many 18-alkylestrane compounds are described with various hormonomimetic properties. These compounds are usually found to have a stronger activity than the corresponding 13-methyl compounds.

The natural steroid hormones have a methyl group in the 13-position. It is only by way of exception that this methyl group is substituted, such as in aldosterone. Most synthetic 19-nor-steroids that have found therapeutic application, are prepared on an industrial scale by starting from natural steroids, modifying and/or eliminating the substituents present in the steroid skeleton and/or introducing substituents into the steroid and/or introducing or saturating double bonds. In these reactions the 13-methyl group is left unaffected. Up to now the 18-alkyl-estrane compounds have been obtained by total synthesis whereby the steroid skeleton is built up from smaller molecules and the 18-alkyl group is built in by proper choice of the starting substances. The total synthesis is a long and laborious procedure, particularly due to the presence of the many asymmetric carbon atoms in the steroid skeleton. It is true that many synthetic problems have been solved by a suitable choice of starting substances and by finding stereospecific reactions, but nevertheless many isomer separations and purification steps are still imperative, owing to which the yields are low and the costprice relatively high. This might likewise be a reason why 18-alkyl-estrane compounds in spite of the promising properties and strong activities which are mentioned in literature for these compounds, have in fact found so little actual application.

The novel process for the preparation of 11β-hydroxy-18-alkyl-estrane compounds consists therein that (a) the starting substance is an 11β-hydroxy-13-methyl-gonane compound, (b) this steroid is reacted with an acylhypoiodite and (c) the thus obtained 11β-hydroxy-13-iodomethyl-gonane compound, after protection of the 11β-hydroxy group, is reacted with an alkylhalide in the presence of an alkali metal or with an alkali metal alkyl compound or with dimethylformamide in the presence of an alkali metal alkyl compound followed by a treatment with a proton-donor, whereafter in the latter case the 18-carbaldehyde obtained is reduced to the 18-methyl compound or is reacted with a trialkyl- or triarylalkylidene phosphorane (Wittig reagent), followed by a reduction of the thus obtained 18-alkenyl-compound to the corresponding 18-alkyl-compound.

In this manner 11β-hydroxy-18-alkyl-estrane compounds can be prepared in an elegant and simple way without stereoisomeric problems and with good to excellent yields, which compounds hitherto could only be prepared along the more difficult route of the total synthesis.

Advantages of starting with 11β-hydroxy-13-methyl-gonane compounds are that the presence of the 11β-hydroxy groups affords the possibility of functionalising the 13-methyl group by the reaction with an acylhypoiodite and the possibility of preparing 11-substituted 18-alkyl compounds in an easier way then by total synthesis.

The 11β-hydroxy-13-methyl-gonane compounds to be used as starting substances may have substituents in other positions in the ring-system, such as oxo groups (and preferably functional derivatives thereof) in the 3 and/or 17 position; free, esterified or etherified hydroxyl groups in the 1, 2, 3, 4, 5, 6, 7, 15 and/or 16 position, of which the free hydroxyl groups are preferably protected during the process of the invention; alkyl groups such as methyl or ethyl groups in the 1, 6, 7, 9, 11α and or 16 position; and/or a saturated or unsaturated alkyl group with 1–4 C-atoms, such as methyl, ethyl, isopropyl, vinyl, ethynyl, isopropenyl, propadienyl or butenynyl, in the 17α-position, next to a free, esterified or etherified hydroxyl group in the 17β-position. By functional derivatives of oxo groups are meant ketalised oxo groups or oxo groups converted into enol derivatives thereof such as enol-ethers or enol-esters. Furthermore the starting substances may also have double bonds, for example in the 4, 5-, 5,6- or 5,10-positions.

Preferred starting substances are 11β-hydroxy-13-methyl-gonane compounds having the formula:

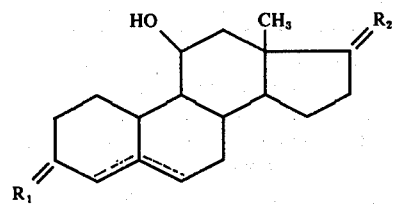

wherein
R₁ = H₂, H(OR₃), O or ketalised O;
R₂ = O, ketalised O, H(OR₄) or (α-alkyl)(βOR₄), the alkyl group having 1–4 C-atoms and R₃ and R₄ being H or a protecting group such as acyl or alkyl, preferably acetyl; and
a double bond is present in the position 4,5 or 5,6.

Specific examples of starting substances are: 11β-hydroxy-Δ⁵-estrene-3,17-dione 3,17-diethylene ketal, 11β,17β-dihydroxy-Δ⁵-estren-3-one 3-ethylene ketal 17-acetate, 11β-hydroxy-Δ⁴-estren-17-one 17-ethylene ketal, Δ⁴-estrene-11β,17β-diol 17-acetate, 11β-hydroxy-Δ⁴-estrene-3,17-dione, 3β,11β-dihydroxy-Δ⁵-estren-17-one 3-acetate 17-ethylene ketal, 11β-hydroxy-Δ⁵-estren-17-one 17-ethylene ketal, Δ⁵-estrene-11β,17β-diol 17-acetate, 11β,17β-dihydroxy-17α-methyl-Δ⁵-estren-3-one 3-ethylene ketal 17-acetate and the corresponding 17α-ethyl compound, etc.

Known estrane compounds without 11β-hydroxy group can be easily converted into starting substances for the process according to the invention by introducing, for example in a microbiological way, an 11α-hydroxyl group, using e.g. the micro-organism *Aspergillus ochraceus*, *Rhizopus nigricans* or *Pestalotia royena* and then oxidizing the 11α-hydroxyl group, for example with chromic acid, to the 11-ketone, whereafter the 11-ketone is converted into the 11β-hydroxy-estrane compound by reduction, for example, with NaBH₄. Thus, 19-nortestosterone, for example is converted into 11α-hydroxy-19-nor-testosterone via the microbiological route and last-mentioned compound is reacted with Jones' reagent to the corresponding 11,17-diketone ($\Delta^4$-estrene-3,11,17-trione), whereafter this 3,11,17-triketone after protection of the 3- and 17-oxo group in the form of a ketal, is converted into 11β-hydroxy-$\Delta^5$-estrene-3,17-dione 3,17-diketal by reduction with $NaBH_4$.

The 11β-hydroxy group may also be introduced directly along the microbiological route, for example with the micro-organism *Curvularia lunata*.

The 11β-hydroxy-13-methyl-gonane compounds to be used as starting substances are reacted in the first reaction step according to the invention with an acyl hypoiodite to give an 11β-hydroxy-13-iodo-methylgonane compound. The acylhypoiodite is preferably formed in situ from iodine and an acylate of a heavy metal, such as the acetates, propionates or benzoates of the metals of the first, second and fourth side-group of the Periodic System, e.g. the silver, mercury and lead acylates. Preferably a lead tetra-acylate, such as lead tetra acetate, is used, which forms with iodine a lead di-acylate and an acylhypoiodite. The acylhypoiodite converts the 11β-hydroxy group into the 11β-hypoiodite group, whereafter by way of an intramolecular conversion the 11β-hydroxy-13-iodomethyl compound is formed.

This step is preferably performed by dissolving or suspending the starting substance in a solvent inert with regard to the reactants, for example in a hydrocarbon, such as cyclohexane or methylcyclohexane, or in a chlorinated hydrocarbon, such as dichloromethane, carbon tetrachloride or hexachlorobutadiene, adding lead tetra-acetate and iodine and if necessary a weak alkali, such as e.g. calcium carbonate, and heating the reaction mixture while stirring. The reaction can be performed at normal pressure or raised pressure and, for example, at the boiling temperature of the solvent under reflux. The duration of the reaction depends i.a. on the temperature and on the solvent used. When working with iodine and lead tetra acetate in cyclohexane under reflux, the reaction is completed within one hour as a rule. The temperature is usually kept between 50° C and 150° C.

An acceleration of the reaction can be achieved by irradiating the reaction mixture with visible and/or ultra violet light. However, preferably a radical initiator is added to the reaction mixture for that purpose. Addition of, for example, azoisobutyrodinitril turned out to influence the duration of the reaction very favourably. The amount of radical initiator is not very critical. With a quantity of 0.1–0.25 gmol per gmol steroid excellent results are achieved.

So as to obtain a good yield, the amount of iodine in the reaction mixture should be such that per gmol steroid at least 0.5 gmol $I_2$ is present. Preferably a certain excess of $I_2$ is used, however, usually not exceeding 1.5 gmol $I_2$ per gmol steroid. The amount of lead tetra acylate, expressed in gmol, should at least be equal to the amount of $I_2$, but is preferably greater. Usually 1.5–3 gmol lead tetra acylate is used per gmol $I_2$.

The duration of the reaction is closely connected with the amount of iodine used. In case of a greater excess of iodine the reaction time should be shortened to avoid that the 11β-hydroxy-13-iodomethyl compound is reacting again, forming via the 11β-acylhypoiodite thereof the 11β-hydroxy-13-diiodomethyl compound. The formation of last-mentioned compound would unfavourably influence the yield of the desired 11β-hydroxy-13-iodomethyl compound, as a matter of course.

In boiling cyclohexane and in the presence of a radical initiator the duration of reaction will, in case of an amount of 0.5–1.0 gmol $I_2$ per gmol steroid, be between about 10 and about 30 minutes; in case of an amount of about 1.5 gmol $I_2$ per gmol steroid, the reaction will have been completed in a few minutes.

Of the 11β-hydroxy-13-iodomethyl-gonane compound obtained in the first step, the 11β-hydroxy group is then protected temporarily. This can be done effectively in the form of an ether. Protection as ester is not effective, because under the circumstances of the next reaction step, an ester group will also react.

As protective ether, the trimethylsilylether turned out to give excellent satisfaction. The etherification is, for example, performed by reacting the 11β-hydroxy-steroid with trimethylchlorosilane in a solvent, such as e.g. pyridine, and at a low temperature.

According to the method of the invention, the 11β-ether of the 11β-hydroxy-13-iodomethyl-gonane compound is then reacted with an alkylhalide in the presence of an alkali metal or with an alkali metal alkyl compound or is reacted with dimethylformamide in the presence of an alkali metal alkyl compound, followed by a treatment with a proton-donor.

Preferably an alkyliodide is used as alkylhalide. The alkali metal is preferably sodium. Examples of alkyl iodides which are preferably used are the alkyl iodides with 1–4 C-atoms, such as methyliodide, ethyliodide, propyliodide, butyliodide, isobutyliodide.

As alkali metal alkyl compound, preferably an alkyllithium compound is used. Examples of these compounds preferably used are the alkyllithium compounds with 1–4 C-atoms, such as methyllithium, ethyllithium, butyllithium.

The reaction with the alkylhalide in the presence of sodium or with the alkyllithium compound is performed in a solvent under anhydrous conditions at normal temperatures, for example in dry ether or dry tetrahydrofuran, and in a nitrogen atmosphere. In this manner the 11β-ether of the corresponding 11β-hydroxy-18-alkyl-estrane compound is obtained from the 11β-ether of the 11β-hydroxy-13-iodomethyl-gonane compound.

The ether group in the 11-position can be removed by hydrolysis, for example by treatment with hydrochloric acid in acetone.

In case of the reaction with dimethylformamide the same compounds as mentioned above are used as alkali metal alkyl compound, for example methyllithium or butyllithium. The reaction is performed at room temperature under anhydrous conditions in an inert solvent, for example diethylether or hexane. The thus-formed dimethylaminocarbinol compound in the form of the lithiumalkoxide is then decomposed to the 18-carbaldehyde by means of a proton donor. As proton donor, water satisfies. Also a diluted ammonium chloride solution can be used or optionally an organic acid, such as oxalic acid. The decomposition reaction is suitably performed by pouring out the reaction mixture of the dimethylformamide reaction into water, optionally containing dissolved ammonium chloride or oxalic acid. The 18-carbaldehyde is extracted, for example with methylene chloride, the extract is evaporated and the residue is purified, if desired, for example by chromatography.

The 11β-hydroxy-18-carbaldehyde compound may also be present in its isomeric form, the (18α → 11β)-carbolactol (the cyclic hemi acetal) with which it is in equilibrium.

The 18-carbaldehyde is then reduced to the 18-methyl compound or optionally reacted first with Wittig reagent to give an 18-alkenyl compound, which is then reduced to the 18-alkyl compound.

The reduction is performed effectively according to the method of Wolff-Kishner, whereby the carbonyl compound is converted into the hydrazone or semicarbazone thereof and the hydrazone or semicarbazone is decomposed with alkali. This decomposition is performed with the aid of potassium hydroxide or with an alkoxide, such as e.g. sodium ethoxide. Preferably the Huang-Minlon modification is used, whereby the decomposition is performed in a highly boiling solvent, such as diethylene glycol and the water formed during the reaction is distilled off.

The optional reaction of the 18-carbaldehyde with Wittig reagent (a triaryl- or trialkyl-alkylidene phosphorane), for example with triphenylmethylene phosphorane or triphenylethylidene phosphorane, said Wittig reagent being prepared in situ from a trialkyl- or triarylphosphine, for example triphenylphosphine, and an alkylhalide, for example methyl- or ethylbromide, with the aid of a suitable base, such as butyllithium, ethylmagnesiumbromide, dimethylsodiumamide or dimsylsodium, is performed in a suitable solvent, such as dimethylsulphoxide, diethylether, dioxane or tetrahydrofuran.

The thus-obtained 18-alkenyl compound is finally converted into the alkyl-estrane compound, that can be done effectively by reduction in a suitable solvent, such as tetrahydrofuran or methanol, with hydrogen in the presence of a noble metal catalyst, for example Pd/BaSO$_4$ or Adams catalyst (PtO$_2$), preferably also in the presence of a small amount of acetic acid.

The 11β-hydroxy-18-alkyl-estrane compounds prepared by the process of the invention can easily be converted into important known compounds such as, for example, 17α-ethinyl-17β-hydroxy-18-methyl-Δ$^4$-estren-3-one (= norgestrel) and 11-methylene-17α-ethinyl-17β-hydroxy-18-methyl-Δ$^4$-estren-3-one, both being very active progestational compounds. For preparing known 11-unsubstituted compounds, the 11β-hydroxy group is oxidised with chromic acid or by the Oppenauer oxidation method and the 11-oxo group thus-obtained is reduced by the method of Wolff-Kishner, whereafter substituents required elsewhere in the molecule are introduced according to methods known per se, such as the introduction of a 17α-ethinyl-17β-hydroxy group in a 17-ketone by the well-known reaction with potassium acetylide. For preparing 11-methylene compounds, the 11β-hydroxy group is also oxidised as indicated above and the 11-oxo group thus obtained is reacted, for example, with triphenylphosphorylmethylene (Wittig reagent) to give the 11-methyleen group. (See for example South African Patent No. 73/9161).

The 18-iodo and 18-carbaldehyde compounds obtained according to the invention as intermediates are novel. Thus, the invention therefore also relates to novel intermediates having the general formula:

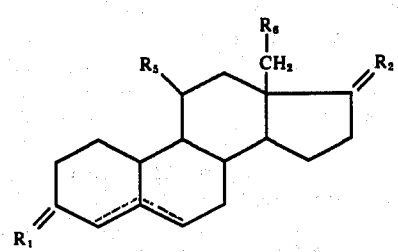

wherein R$_1$ and R$_2$ have the meanings as given hereinbefore; R$_5$ = a free, esterified or etherified hydroxyl group; R$_6$ = I or

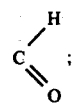

and a double bond is present in the 4,5- or 5,6-position.

An ester group that may be present is derived from an organic carboxylic acid with 1–18 C-atoms. An ether group, if present, is, for example, the methylether-, the ethylether-, the tetrahydropyranylether- or the trimethylsilylether-group. A ketal group, if present, is, for example, the ethylene ketal or dimethylketal group.

These novel compounds are not only important intermediate products for the preparation of pharmacologically important 18-alkyl-estrane compounds, but have also interesting estrogenic, progestative, ovulation-inhibiting and peripheral anti-fertility properties.

The invention will be further illustrated with the following examples:

EXAMPLE I a. 19.8 g of lead tetra acetate (3 × washed with cyclohexane) and 3.87 g of iodine were suspended in 350 ml of cyclohexane. The mixture was refluxed for 20 minutes and then cooled down to room temperature. Then 9.9 g of 11β-hydroxy-Δ$^5$-estrene-3,17-dione 3,17-diethylene ketal and 0.69 g of azo-isobutyrodinitril were added whereafter the mixture was refluxed for another 20 minutes. The reaction mixture was filtrated on hyflo and the filtrate washed with water to neutral. The organic layer was dried on Na$_2$SO$_4$, filtered and concentrated in vacuo until dry. Weight of the residue: 12.65 g. The residue was taken up in 25 ml of ethanol and put aside for one night at −20° C. The crystals formed were filtered off and dried. In this way 6.21 g of 11β-hydroxy-18-iodo-Δ$^5$-estrene-3,17-dione 3,17-diethylene ketal were obtained. Melting point: 143°–144° C.

In a similar manner 11β,17β-dihydroxy-Δ$^5$-estren-3-one 3-ethylene ketal 17β-acetate, Δ$^4$-estrene-11β,17β-diol 17β-acetate, 11β-hydroxy-Δ$^5$-estren-17-one 17-ethylene ketal and 11β,17β-dihydroxy-17α-methyl-Δ$^5$-estren-3-one 3-ethylene ketal 17β-acetate were converted into the corresponding 18-iodo compound.

b. 6.2 g of 11β-hydroxy-18-iodo-Δ$^5$-estrene-3,17-dione 3,17-diethylene ketal were dissolved in 42 ml of dry pyridine. The solution was cooled to 0° C and then 6 ml of trimethylchlorosilane were added in one hour. Subsequently the reaction mixture was stirred for 2 hours at 0° C and then poured out into 0.5 ltr of ice water. The crystals were filtered off and dried in vacuo at room temperature on KOH. In this way 6.44 g of 11β-hydroxy-18-iodo-Δ⁵-estrene-3,17-dione 11β-trimethylsilylether 3,17-diethylene ketal were obtained with a melting point of 153°–155° C. In a similar manner the other 11β-hydroxy-18-iodo-compounds mentioned in example I a) were converted into the corresponding 11β-trimethylsilylethers.

c. To 1.15 g (2 mmol) of 11β-hydroxy-18-iodo-Δ⁵-estrene-3,17-dione 3,17-diethylene ketal 11β-trimethylsilylether in 20 ml of dry THF, 5 ml of 2 N methyllithium were added dropwise while the mixture was kept under N₂. After stirring for 4 hours water was added whereafter the etheric layer was separated and the water layer extracted with ether. The combined organic layers were dried with Na₂SO₄. After evaporation, the residue (0.85 g) was chromatographed on 100 g of SiO₂ with toluene/ethylacetate 9:1 and 2% pyridine as eluent. Obtained: 0.30 g of 11β-hydroxy-18-methyl-Δ⁵-estrene-3,17-dione 3,17-diethylene ketal 11β-trimethylsilylether; melting point 168°–171° C. Treatment with concentrated hydrochloric acid in acetone gave 11β-hydroxy-18-methyl-Δ⁴-estrene-3,17-dione. In a similar manner 11β,17β-dihydroxy-Δ⁵-estren-3-one 3-ethylene ketal 11β-trimethylsilylether 17β-acetate, Δ⁴-estrene-11β,17β-diol 11β-trimethylsilylether 17β-acetate, 11β-hydroxy-Δ⁵-estren-17-one 17-ethylene ketal 11β-trimethylsilylether and 11β,17β-dihydroxy-17α-methyl-Δ⁵-estren-3-one 3-ethylene ketal 11β-trimethylsilylether 17β-acetate gave 11β,17β-dihydroxy-18-methyl-Δ⁴-estren-3-one, 18-methyl-Δ⁴-estrene-11β,17β-diol, 11β-hydroxy-18-methyl-Δ⁵-estren-17-one and 11β,17β-dihydroxy-17α,18-dimethyl-Δ⁴-estren-3-one, respectively.

EXAMPLE II 500 mg (0.88 mmol) of 11β-hydroxy-18-iodo-Δ⁵-estrene-3,17-dione 11β-trimethylsilylether 3,17-diethylene ketal, as obtained in Example I b), were dissolved in 30 ml of dry ether. To this solution 1.0 ml of 20% n-butyllithium in hexane was added under N₂, whereafter the mixture was stirred for 4 hours at room temperature. Water was added and the organic layer was separated. After drying of the organic layer over Na₂SO₄, the mixture was evaporated and the residue chromatographed on 45 g of silicagel with toluene-/ethylacetate 9:1 + 2% pyridine as eluent. The thus-obtained 11β-hydroxy-18-n-butyl-Δ⁵-estrene-3,17-dione 3,17-diethylene ketal 11β-trimethylsilylether was converted with concentrated hydrochloric acid in acetone into 11β-hydroxy-18-n-butyl-Δ⁴-estrene-3,17-dione; melting point 115°–119° C.

In a similar manner the other 11β-trimethylsilylethers prepared in example I b) were converted into 11β,17β-dihydroxy-18-n-butyl-Δ⁴-estren-3-one, 18-n-butyl-Δ⁴-estrene-11β,17β-diol, 11β-hydroxy-18-n-butyl-Δ⁵-estren-17-one and 11β,17β-dihydroxy-17α-methyl-18-n-butyl-Δ⁴-estren-3-one, respectively.

EXAMPLE III a. 1.15 g of 11β-hydroxy-18-iodo-Δ⁵-estrene-3,17-dione 3,17-diethylene ketal 11β-trimethylsilylether were dissolved in 50 ml diethylether dried on KOH. To this solution 2 ml of 1.5 molar butyllithium in diethylether were added while the reaction mixture was stirred for 1 hour at room temperature. Then 1.5 ml of distilled dimethylformamide were added. A sticky precipitate was formed immediately. The mixture was refluxed for another hour. Then the mixture was poured out into water and extracted with CH₂Cl₂. The organic layer was dried on sodium sulphate, filtrated and evaporated in vacuo until dry. The residue (0.9 g) was chromatographed on 27 g of SiO₂ with toluene-/ethylacetate 1:1 + 2% pyridine. In this manner 11β,18a-epoxy-18a-hydroxy-18-methyl-Δ⁵-estrene-3,17-dione 3,17-diethylene ketal (= 11β-hydroxy-18-formyl-Δ⁵-estrene-3,17-dione 3,17-diethylene ketal cyclohemiacetal) was obtained; melting point 144°–146° C (dec.). In a similar manner the other 18-iodo-11β-trimethyl-silylethers obtained in example I b) were converted into the corresponding 11β,18a-epoxy-18a-hydroxy-18-methyl-compounds.

b. 3.4 g of 11β-hydroxy-18-formyl-Δ⁵-estrene-3,17-dione 3,17-diethylene ketal (cyclohemi-acetal) were suspended in 33 ml of 100% ethanol, 80 ml of diethylene glycol and 33 ml of hydrazine hydrate. Then 6.8 g of hydrazine-dihydrochloride were added. The mixture was brought at 100° C and kept at this temperature for 16 hours. After that the reaction mixture was cooled down to room temperature whereafter 12 g of powdered potassium hydroxide and 240 ml of diethylene glycol were added. The reaction mixture was brought at 200° C while distilling off the fractions boiling at lower temperatures. The mixture was kept at 200° C for 1.5 hours and then cooled down to room temperature, poured out into 2.5 ltr of ice-water while stirring and stirred for another hour, whereafter the precipitate formed was filtered off, washed to neutral with water and dried at 70° C in vacuo. After recrystallisation from ethylacetate 2.4 g of 11β-hydroxy-18-methyl-Δ⁵-estrene-3,17-dione 3,17-diethylene ketal were obtained with a melting point of 178°–181° C. In a similar manner the other cyclohemi-acetals obtained in example III a) were converted into the corresponding 11β-hydroxy-18-methyl-compounds.

EXAMPLE IV a. 1.3 g of sodium hydride (suspension in oil (55–60%) were suspended in 25 ml of dry DMSO. The mixture was placed in a waterbath of 75° C for one hour and then cooled down to room temperature. To the cooled mixture a solution of 10.8 g of methyltriphenylphosphoniumbromide in 35 ml of dry DMSO was added. After stirring for 15 minutes at room temperature a suspension of 2.3 g of 11β-hydroxy-18-formyl-Δ⁵-estrene-3,17-dione 3,17-diethylene ketal in 30 ml of dry DMSO was added. The whole mixture was stirred for 6 hours in a waterbath at 50° C and then poured out into 1 litre of ice water. The oily residue was filtered off on hyflo, washed with water and then a few times with cold methanol/H₂O 1:1.

The filter was washed out with methylene chloride, the methylene chloride layer was washed with water, then dried on Na₂SO₄, filtered off and evaporated in vacuo to obtain 2.36 g of 11β-hydroxy-18-vinyl-Δ⁵-estrene-3,17-dione 3,17-diethylene ketal.

In a similar manner, the other 11β-hydroxy-18-formylcompounds obtained in example III a) were converted into the corresponding 11β-hydroxy-18-vinyl compounds.

b. 100 mg of platinum-oxide was pre-hydrogenated for half an hour in a mixture of 40 ml of methanol/tetrahydrofuran 1:1. Then 1 g of 11β-hydroxy-18-vinyl-Δ⁵-estrene-3,17-dione 3,17-diethylene ketal and 0.4 ml of 100% acetic acid were added. The 18-vinyl-compound was hydrogenated at room temperature and at 1 ato. After absorption of 1 mol hydrogen per mol steroid, the catalyst was filtered off and the reaction mixture evaporated. The residue (0.98 g) was purified by chromatography on silicagel (toluene/ethyl acetate 9:1 + 2% pyridine), to obtain 11β-hydroxy-18-ethyl-Δ⁵-estrene-3,17-dione 3,17-diethylene ketal. In a similar manner the other 18-vinyl compounds mentioned in example IV a) were hydrogenated to the corresponding 18-ethyl compounds.

I claim:

1. A process for preparing an 11β-hydroxy-18-alkyl steroid of the estrane series, the alkyl group having 1–4 carbon atoms, which steroid may be substituted in the 3- and/or 17-position by an oxo group or a functional derivative thereof, in the 1, 2, 3, 4, 5, 6, 7, 15 and/or 16-position by hydroxy, acyloxy derived from an organic carboxylic acid having 1–18 carbon atoms, alkoxy having 1–2 carbon atoms, tetrahydropyranyloxy or trimethylsilyloxy, in 1, 6, 7, 9, 11α and/or 16-position with alkyl having 1–2 carbon atoms and in 17α-position with saturated or unsaturated alkyl having 1–4 carbon atoms next to hydroxy, acyloxy derived from an organic carboxylic acid having 1–18 carbon atoms, alkoxy having 1–2 carbon atoms, tetrahydropyranyloxy or trimethylsilyloxy in 17β-position, and may have a double bond in 4,5-, 5,6-, or 5,10-position, which comprises reacting the corresponding 11β-hydroxy-13-methyl-gonane compound with an acyl hypoiodite, reacting the corresponding 11β-hydroxy-13-iodomethyl-gonane compound thus obtained, after protecting the 11β-hydroxy group in the form of an ether, with an alkyl halidem the alkyl group having 1–4 carbon atoms, in the presence of an alkali metal or with an alkali metal alkyl compound, the alkyl group having 1–4 carbon atoms, or with dimethylformamide in the presence of an alkali metal alkyl compound, the alkyl group having 1–4 carbon atoms, followed by a treatment with a proton donor, whereafter in the latter case the thus obtained 18-carbaldehyde group is reduced or reacted with Wittig reagent, followed by reduction of the thus obtained 18-alkenyl group.

2. Process according to claim 1, in which the starting 11β-hydroxy-13-methyl-gonane compound has the formula

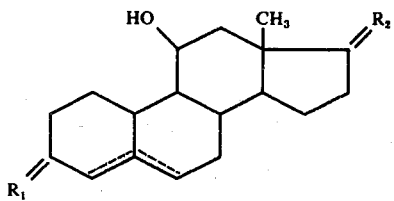

wherein
R₁ = H₂, H(OR₃), O or ketalised O;
R₂ = O, ketalised O, H(OR₄) or (α-alkyl)(βOR₄), the alkyl group having 1–4 C-atoms and R₃ and R₄ being H or a protecting group such as acyl or alkyl; and
a double bond is present in the position 4,5 or 5,6.

3. Process according to claim 2, in which in the formula
R₁ = H₂, H(Oacetyl) or ethylenedioxy; and
R₂ = ethylenedioxy, αH(βOacetyl) or (α-alkyl 1–4 C) (βOacetyl).

4. Process according to claim 1, in which the acylhypoiodite is formed in situ from iodine and an acylate of a heavy metal.

5. Process according to claim 4, in which lead tetra acetate is used as acylate of a heavy metal.

6. Process according to claim 5, in which per gmol steroid 0.5–1.5 gmol iodine is used and at least an equivalent amount of lead tetra acylate.

7. Process according to claim 6, in which per gmol iodine 1.5–3 gmol of lead tetra acylate is used.

8. Process according to claim 1, in which in the first step a cyclic hydrocarbon is used as solvent.

9. Process according to claim 8, in which cyclohexane is used as solvent.

10. Process according to claim 1, in which in the first step the reaction is performed in the presence of a radical initiator.

11. Process according to claim 10, in which azoisobutyrodinitril is used as radical initiator.

12. Process according to claim 1, in which in the 11β-hydroxy-13-iodo-methyl-compound the 11β-hydroxy group is temporarily protected in the form of the trimethylsilylether.

13. Process according to claim 1, in which alkyliodide is used as alkylhalide.

14. Process according to claim 1, in which sodium is used as alkali metal.

15. Process according to claim 1, in which an alkyllithium compound with 1-4 C-atoms is used as alkali metal alkyl compound.

16. Process according to claim 1, in which water is used as proton donor.

17. Process according to claim 1, in which an 18-carbaldehyde compound obtained, is reduced by converting the carbonyl group into the hydrazone or semicarbazone and decomposing this hydrazone or semicarbazone under alkaline conditions.

18. Process according to claim 1, in which an 18-carbaldehyde compound is reacted with a triarylalkylidene phosphorane (Wittig reagent) and the 18-alkenyl compound formed is reduced with hydrogen in the presence of a noble metal catalyst to the corresponding 18-alkyl compound.

19. A compound having the formula

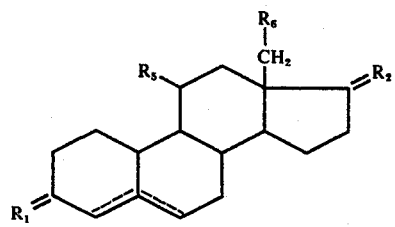

, wherein wherein
R₁ = H₂, H(OR₃), O or ketalised O;
R₂ = O, ketalised O, H(OR₄) or (α-alkyl)(βOR₄), the alkyl group having 1–4 carbon atoms and R₃ and R₄ being H or a protecting group such as acyl or alkyl;
R₅ = OH, acyloxy derived from an organic carboxylic acid having 1–18 carbon atoms, alkoxy having 1–2 carbon atoms, tetrahydropyranyloxy or trimethylsilyloxy;
R₆ = I or

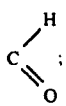
and a double bond is present in the 4,5- or 5,6-position.
20. A compound according to claim 19, wherein
$R_1 = H_2$ or ethylenedioxy;
$R_2 = $ ethylenedioxy or $\alpha H(\beta OAcetyl)$;
$R_5 = $ OH or trimethylsilyloxy; and
$R_6 = $ I or
* * * * *